United States Patent
Platt

(10) Patent No.: US 6,730,025 B1
(45) Date of Patent: May 4, 2004

(54) HAND HELD PHYSIOLOGICAL SIGNAL ACQUISITION DEVICE

(76) Inventor: Harry Louis Platt, 14/166 Belmore Road, NSW, 2031 (AU)

( * ) Notice: Subject to any disclaimer, the term of this patent is extended or adjusted under 35 U.S.C. 154(b) by 0 days.

(21) Appl. No.: 09/831,030

(22) PCT Filed: Nov. 3, 1999

(86) PCT No.: PCT/AU99/00955

§ 371 (c)(1),
(2), (4) Date: Nov. 28, 2001

(87) PCT Pub. No.: WO00/25661

PCT Pub. Date: May 11, 2000

(30) Foreign Application Priority Data

Nov. 3, 1998 (AU) .............................................. PP6868
May 6, 1999 (AU) .............................................. PQ0184

(51) Int. Cl.⁷ ................................................. A61B 5/00
(52) U.S. Cl. ...................... 600/300; 128/920; 600/301; 600/509
(58) Field of Search ................................ 600/300–301, 600/500–508, 509, 523, 529–532, 365, 587–595; 128/903, 904, 920–925; 340/573.1; 705/2–4; 463/48; 379/106.1–106.2; 700/90–92

(56) References Cited

U.S. PATENT DOCUMENTS

| | | | | | |
|---|---|---|---|---|---|
| 5,307,263 A | * | 4/1994 | Brown | .................. | 600/301 |
| 5,876,351 A | * | 3/1999 | Rohde | .................. | 600/523 |
| 5,899,855 A | * | 5/1999 | Brown | .................. | 600/301 |
| 5,961,451 A | * | 10/1999 | Reber et al. | .................. | 600/322 |

* cited by examiner

Primary Examiner—Max F. Hindenburg
Assistant Examiner—Michael Astorino
(74) Attorney, Agent, or Firm—Edwin D. Schindler

(57) ABSTRACT

A hand held, portable and multipurpose medical device for biological signals acquisition, display and storage. The device includes a multipurpose computerized apparatus (2) which is primarily used for computer games as well as a biological signals acquisition module (1) which uses a plurality of biological sensors (6). A cartridge (4) used in conjunction with the computerized apparatus is preprogrammed and includes a read only memory (ROM) for storage of the program and a random access memory (RAM) for storage of acquired data. The acquired data in one form is an ECG and the apparatus simultaneously acquires and displays the ECG waveform in "real time". Multiple memories in the apparatus are used for storage of the acquired ECG and to enable output to a printer (8) for hard copy or to a PC for analysis and reporting.

12 Claims, 3 Drawing Sheets

HAND HELD PHYSIOLOGICAL SIGNAL ACQUISITION DEVICE

The present invention relates to physiological monitoring of patients and, in particular, to physiological signal acquisition apparatus which provides real time and/or simultaneous transmission and display of the acquired signals via a hand held electronic machine/display.

BACKGROUND TO THE INVENTION

Shifts in patient care, practices are changing the nature of monitoring. Increasingly, hospitals are attempting to lower costs by moving high-acuity patients as quickly as possible from intensive care units (ICU) to intermediate care and general ward areas.

This trend has dramatically reduced the need for the high end stationary, multi-parameter monitoring systems typically employed in the ICU. This has intensified demand for a more flexible, and therefore less expensive, systems that can easily be integrated into lower-acuity areas and configured to individual patient needs.

This is particularly the case in heart monitoring where the ECG is the well known form of monitoring.

Clinicians require rapid, sophisticated monitoring capability without compromising diagnostic quality and at low cost. Therefore it would be advantageous to provide a physiological signal monitor which is capable of providing real time acquisition and display of acquired signals via a portable, hand held electronic machine/display.

OBJECT OF THE INVENTION

It is an object of the present invention to provide a physiological signal acquisition and display apparatus which substantially overcomes or ameliorates the above mentioned disadvantages. At the very least, the object of the invention is to provide an alternative to known physiological signal acquisition and display apparatus.

DISCLOSURE OF THE INVENTION

According to one aspect of the present invention there is disclosed a portable and multipurpose medical device for biological signals acquisition, display and biological data storage, said device comprising:
 a preprogrammed cartridge comprising:
  a housing;
  a connector partially disposed within the housing;
  a read only memory (ROM) for storage of the program which has been preprogrammed;
  a random access memory (RAM) for storage of acquired data;
  a ROM—RAM parallel interface; and
 a portable device comprising:
  a second housing;
  a slot connector being provided for insertion of the pre-programmed cartridge;
  a display screen being provided on the second housing for displaying the acquired data;
  a joy pad and control buttons disposed within the second housing to control data acquisition options, horizontal and vertical scales of the display, and other application specific functions of the medical device; and
 a biological signals acquisition module comprising:
  a third housing;
  a plurality of biological sensors;
  an analog circuit to amplify and pre-condition biological signals from the plurality of the biological sensors;
  input/output interface to connect said third housing to said second housing;
  a digital circuit for digitizing the biological signal and to send the biological data through the connector regarding the biological data means for storing the collected biological data in the RAM of the first housing.

According to another aspect of the present invention there is disclosed a portable and multipurpose medical device for biological signals acquisition, display and biological data storage, said device comprising:
 a preprogrammed and a biological signals acquisition module comprising:
  a housing;
  a connector partially disposed within the housing;
  a read only memory (ROM) for storage of the program which has been preprogrammed;
  a random access memory (RAM) for storage of acquired data;
  a ROM-RAM parallel interface;
  a plurality of biological sensors;
  an electrically isolated analog circuit to amplify and pre-condition biological signals from the plurality of the biological sensors;
  a digital circuit for digitizing the biological signal and to send the biological data through the connector regarding the biological data means for storing the collected biological data in the RAM; and
 a portable device comprising:
  a second housing;
  a slot connector being provided for insertion of the pre-programmed module;
  a display screen being provided on the second housing for displaying the acquired data;
  a joy pad and control buttons disposed within the second housing to control data acquisition options, horizontal and vertical scales of the display, and other application specific functions of the medical device.

Preferably, the display device is a hand-held computer display device, for example, a "NINTENDO GAMEBOY" (a registered trademark of Nintendo Co. Ltd., of Kyoto, Japan, for one particularly well-known type of hand-held computer display device) or similar apparatus.

Preferably, the physiological signal acquisition monitoring and display apparatus is used to simultaneously acquire and physiological signals from a plurality of sensors measuring at least one of the group including multilead ECG, FECG, EEG, EMG, oximetry, blood pressure whether detected by invasive or non-invasive means, respiration, temperature, phonocardiogram, tokolytic, blood glucose, $pCO_2$, $pO_2$ and pacemaker pulses, and condition the signals and transmit data representing the signals in real time to an input/output port of the display device.

Preferably, the circuit means includes an isolated section, a non-isolated section with an isolation barrier therebetween, the isolated section being isolated from the input/output port of the display device. The isolated section receives the signals from the sensors and amplifies and preconditions the signals into data specific to the signal type prior to transmitting the data through the isolation barrier.

Preferably, the non-isolated section receives the data transmitted through the isolation barrier and prepares the data for transmission to input/output port of the display device via an input/output interface in the first housing and a cable means to the input/output port of the display device which is a second housing of the apparatus.

Preferably, the second housing is the Nintendo Game Boy® apparatus which comprises a microprocessor module, a display module, control means for using internal data and program memory or providing connection to an external data and/or program memory, single or multiple input/output ports, display control and control devices.

Preferably, a Nintendo® Game Boy® video game system is used as the display and control platform for various types of physiological data acquisition devices.

When a new acquisition device is required it simply requires design of the acquisition hardware and associated application software to make a new product. To enable this the application software for each device type is written and stored in game module (CART) ROM.

The final product consists of the acquisition hardware (Acquisition Unit), associated application software embedded in a game CART and the Game Boy® itself.

The Game Boy® combines a display/control system with an I/O interface to create a pocket size, low cost, diagnostic monitor.

BRIEF DESCRIPTION OF THE DRAWINGS

The present invention will be now be described with reference to the accompanying drawings in which.

BEST MODE OF CARRYING OUT THE INVENTION

In the preferred embodiment of the invention a Nintendo® Game Boy® video game system is used as the display and control platform for the acquisition of the electrocardiogram (ECG). The Nintendo® Game Boy® device platform is manufactured and sold by Nintendo Co. Ltd., of Kyoto, Japan.

The electrocardiogram (ECG) is acquired from surface electrodes placed on the thorax in "standard monitoring" configuration or from direct contact to the thorax.

The Nintendo® Game Boy® device using an ECG application CART ie ROM containing pre-programmed software for ECG storage and display when combined with an ECG acquisition module acquires the ECG while simultaneously displaying the ECG waveform in "real time". Multiple memories in the Nintendo® Game Boy® device are used for storage of the acquired ECG. The memories also allow for the stored ECG to be outputted to a printer for hard copy or to a PC for analysis and reporting.

The invention, however, is not limited to acquisition of ECG signals only. For example, FECG, EEG, EMG, oximetry, blood pressure whether detected by invasive or non-invasive means, respiration, temperature, phonocardiogram, tokolytic, blood glucose, pCO2, pO2 and pacemaker pulses.

In the preferred embodiments of the invention a handheld ECG monitoring system with the following characteristics is implemented:

| | |
|---|---|
| Sample Rate: | 200 Hz |
| Resolution: | 8 bit - 26 uV per bit |
| Frequency response: | 0.05 Hz - 100 Hz |
| Hardware Gain: | 755 |
| ECG Storage: | Single memory, 45 second duration, non-volatile, stored on game cart. |

Figure 1:
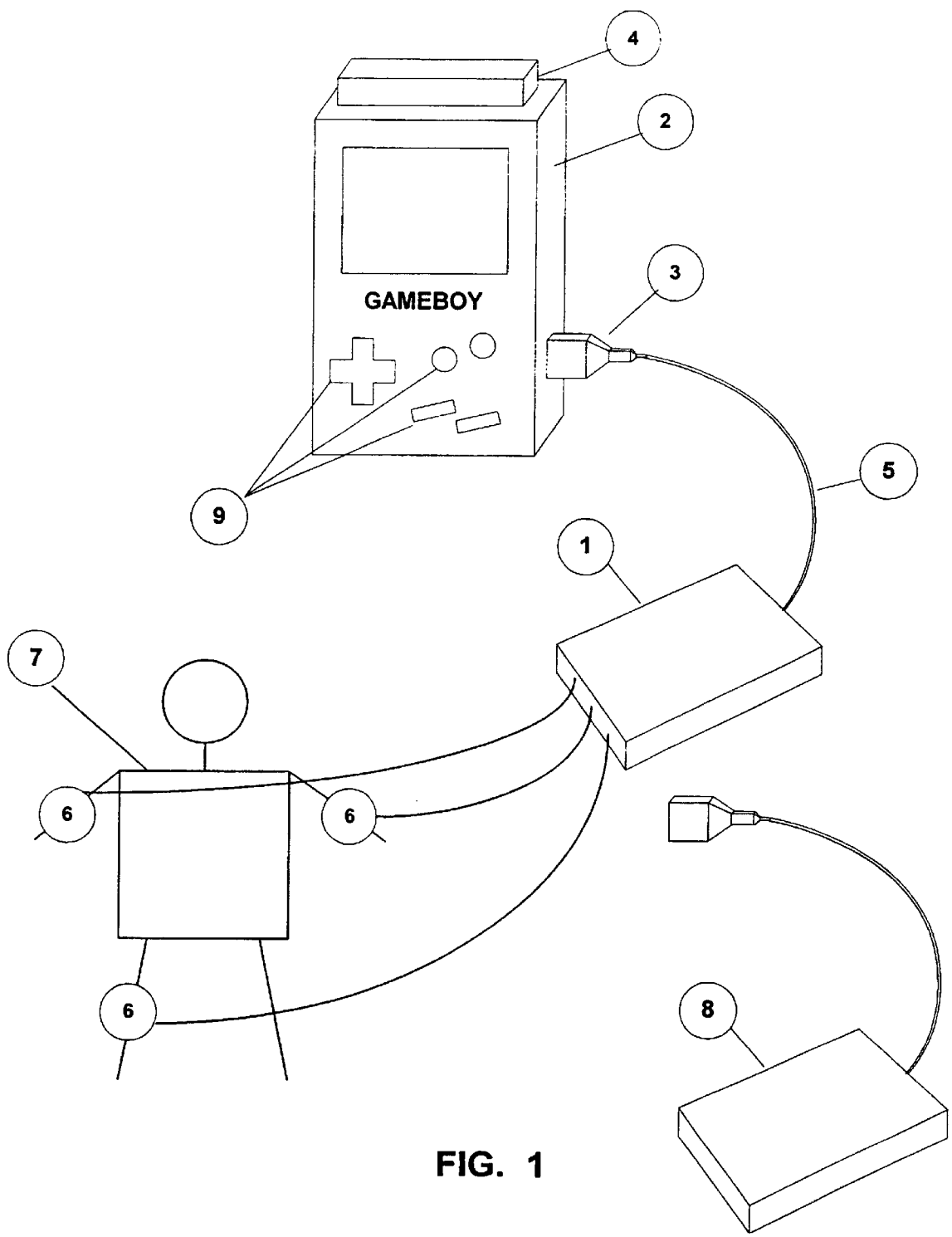
FIG. 1 is a diagram of the utilization of a portable ECG device according to a preferred embodiment.

Referring to FIG. 1, a diagram of the operation of a portable ECG device according to a preferred embodiment is shown. The device includes an ECG acquisition module 1, a Nintendo® Game Boy® video game device 2 and a connector 3 to the serial port of the Nintendo® Game Boy® video game device 2. A pre-programmed cartridge 4 is inserted into the slot of the Nintendo® Game Boy® video game device 2 while the ECG acquisition module 1 is connected via a cable 5 and the connector 3 to the serial port of the Nintendo® Game Boy® video game device 2. The ECG acquisition module 1 has a plurality of biological sensors 6.

ECG signals are collected via the sensors 6 from a patient 7 and after processing by the ECG acquisition module 1 are sent to the serial port of the Nintendo® Game Boy® video game device 2 via cable 5 and connector 3.

An application specific program is stored in the pre-programmed cartridge 4. The program controls ECG data retrieval from the ECG acquisition module 1, data storage, display, printout, user interface and sound functions of the Nintendo® Game Boy® video game device 2.

Acquired data can be displayed in real time, stored in the memory and printed using a Nintendo® Game Boy® printer 8.

Using control buttons 9, the user can adjust horizontal and vertical scale of the display, freeze the picture, review recorded portions of the signal, enable or disable recording, initiate printout etc.

The configuration shown in FIG. 1 provides a diagnostic medical tool with functionality defined by the pre-programmed cartridge 4 and by the acquisition module 1.

Figure 2:
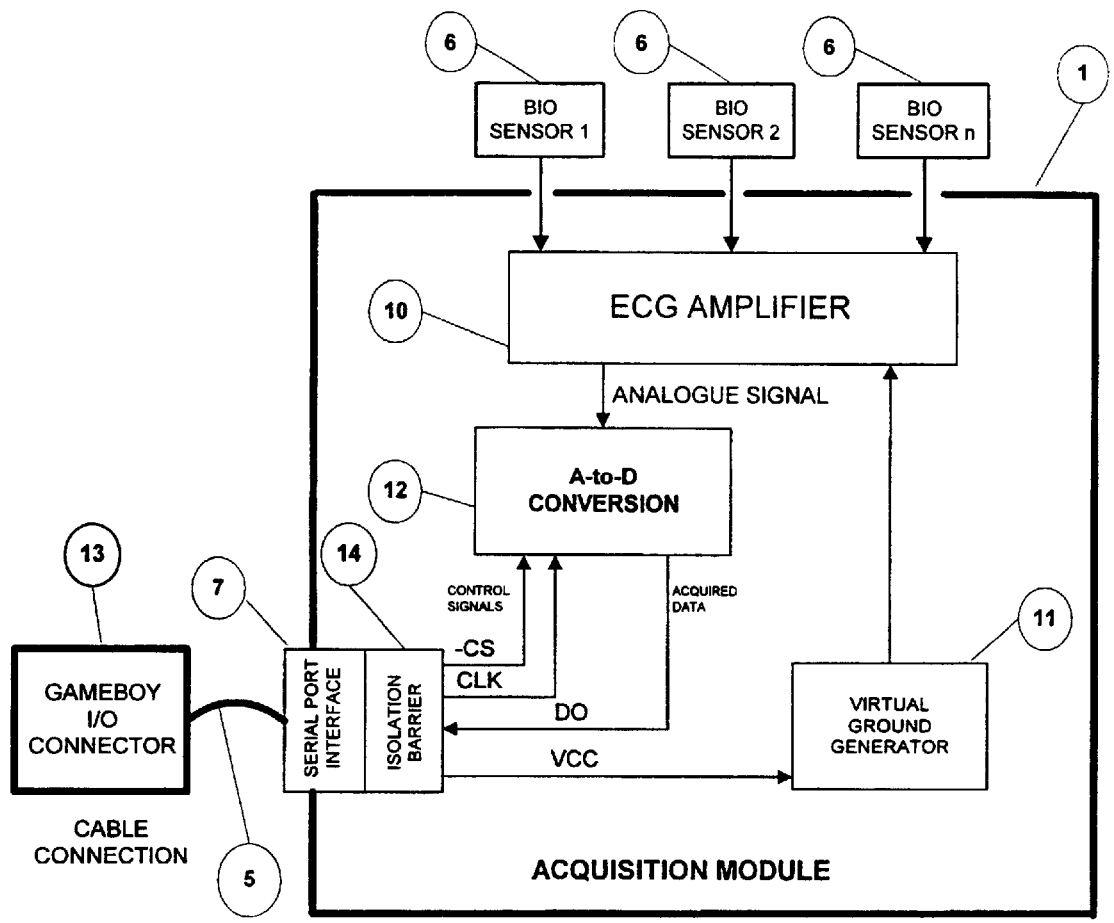
FIG. 2 is a block diagram of an ECG acquisition module of the medical device connected to the serial connector of Nintendo® Game Boy® video system device according to a preferred embodiment of the invention.

A block diagram of ECG acquisition module is shown in FIG. 2. The ECG signal is collected via the sensors 6 and amplified by amplifier 10. The amplifier 10 is DC biased by the virtual ground potential produced by the virtual ground generator 11. The amplified analogue signal is fed to the input of analogue to digital converter (ADC) 12. The ADC 12 has two control inputs (-CS and CLK) and one output (DO). Control signals -CS and CLK are supplied by the Nintendo® Game Boy® device 2 via its serial port, the connector 3 and the cable 5 to a serial port interface 13 of the ECG acquisition module 1.

The amplified analogue signal is converted into digital ECG data (DO) and sent to the RAM of the pre-programmed cartridge 4 via the serial port interface 13 of the ECG acquisition module 1, the cable 5, the connector 3 and internal circuitry of the Nintendo® Game Boy® device 2.

Digital ECG data being stored in the RAM are accessible for displaying, calculations and overwriting. Control and data signals flow is defined by the program stored in the ROM of the pre-programmed cartridge 4.

Figure 3:
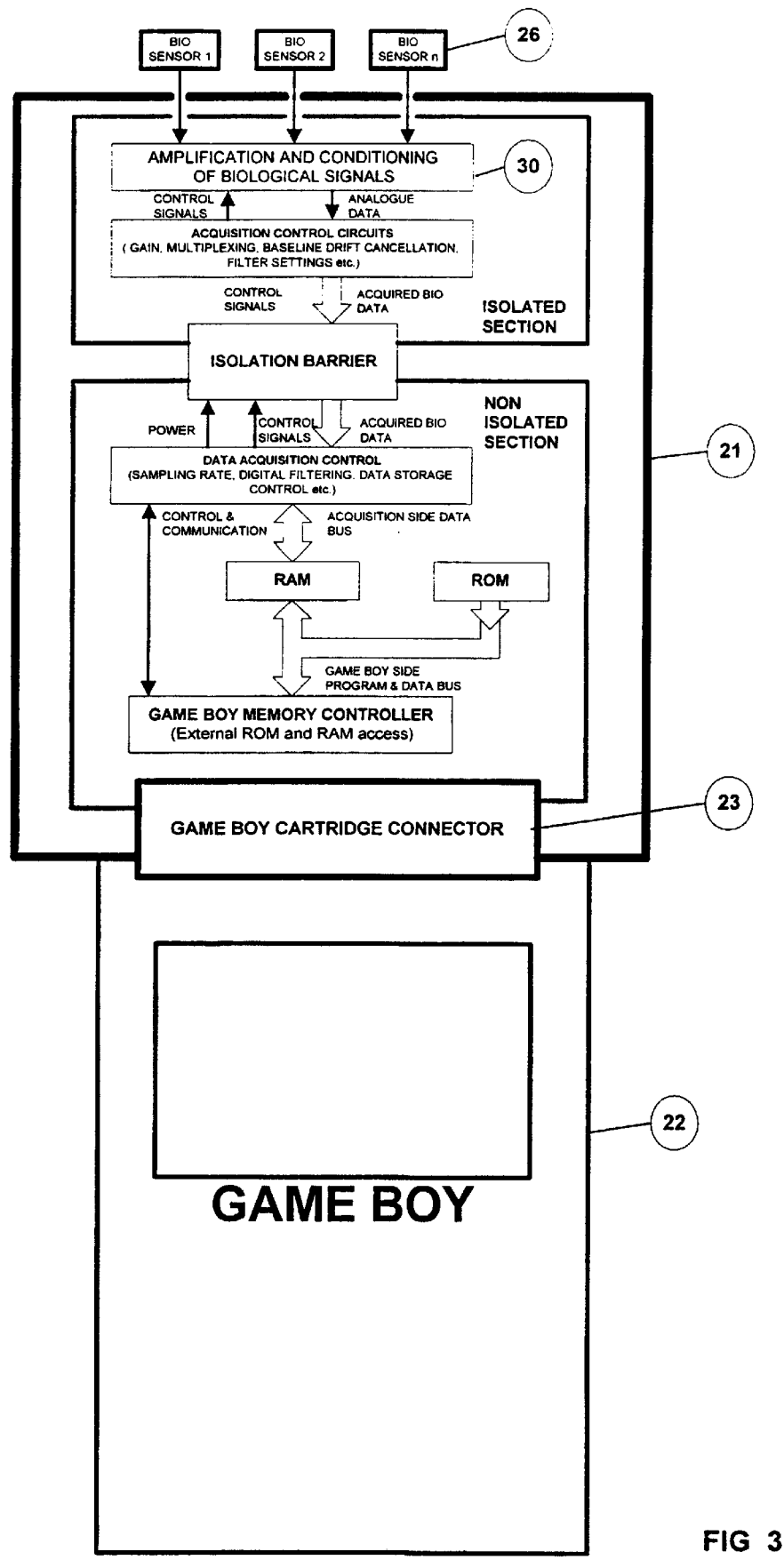
FIG. 3 is a block diagram of an ECG acquisition module of the medical device collected to the Nintendo® Game Boy® video system device according to another preferred embodiment of the invention.

Referring to FIG. 3, a diagram of the operation of a portable ECG device according to another preferred embodiment is shown. The device includes an ECG acquisition module 21, a Nintendo® Game Boy® video game device 22 and a connector 23 to the cartridge port of the Nintendo® Game Boy® video game device 22. The acquisition module 21 includes the pre-programmed cartridge which is inserted into the slot of the Nintendo® Game Boy® video game device 22. The ECG acquisition module 21 has a plurality of biological sensors 26.

ECG signals are collected via the sensors 26 from the patient and after processing by the ECG acquisition module 21 are sent to the Nintendo® Game Boy® video game device 22 via its cartridge connector port.

An application specific program is stored in the pre-programmed cartridge. The program controls ECG data retrieval from the ECG acquisition module 21. data storage, display, printout, user interface and sound functions of the Nintendo® Game Boy® video game device 22.

Acquired data can be displayed in real time, stored in the memory and printed using of Nintendo® Game Boy® printer 8.

Using control buttons 9, the user can adjust horizontal and vertical scale of the display, freeze the picture, review recorded portions of the signal, enable or disable recording, initiate printout etc.

The configuration shown in drawings provides a diagnostic medical tool with functionality defined by the pre-programmed cartridge of the acquisition module 1.

A block diagram of ECG acquisition module is shown in FIG. 3. The ECG signal is collected via the sensors 26 and amplified by amplifier 30.

Digital ECG data being stored in the RAM are accessible for displaying, calculations and overwriting. Control and data signals flow is defined by the program stored in the ROM of the pre-programmed cartridge 21.

Hardware Implementation

The ECG amplifier 10 is comprised of a high input impedance front stage voltage followers, instrumentation amplifier high pass filter, second amplification stage and a low pass anti-aliasing filter.

Front stage voltage followers use popular LMC6464 operational amplifier from National Semiconductors with input current less than 1 nA.

It is believed that the preferred embodiment as described meets AAMI/ANSI ECG recommended safety standards which will include an electrical isolation barrier 14 as seen in FIG. 2.

All digital signals are transferred via digital optical isolators. A high pass filter defines the low end of the frequency band of the acquired ECG signal at 0.05 Hz. A low pass filter removes high frequency noise on the input of ADC. Frequency response of the ECG amplifier 15 selected for 0.05 Hz–100 Hz. 100 Hz high end frequency is defined by the selected sample rate of 200 Hz is in a compliance with the AAMI/ANSI ECG recommended frequency response standards.

The ECG acquisition module 1 uses single positive voltage derived from Nintendo® Game Boy® device serial connector.

In order to amplify bipolar AC ECG signal without distortions, input stage voltage followers and instrumentation amplifier are referenced to AMP_REF voltage=VCC/2 generated by the virtual ground generator 11.

Software Implementation

The software stored in the ROM of the pre-programmed cartridge 4 is executed by the microprocessor of the Nintendo® Game Boy® device 2. In the Nintendo® Game Boy® device 2, the processor is eight-bit microprocessor running at 4.19 MHz. Some of the peripheral functions such as serial communication (SPI), sound generation and local ROM are implemented in the hardware of the microprocessor.

The software in a preferred embodiment is written in C and compiled using the modified GNU compiler in the GameBoy SDK.

The following documents are used for Nintendo® Game Boy® application software development:

Pan of ATX—Marat Fayzullin, Pascal Felber, Paul Robson Martin Korth—May 3, 1998 Thorough description of GB hardware and software interface.

GameBoy Developer's Kit—V2.0.15. Pascal Felber Michael Hope May 10, 1998

GameBoy Assembly Language Commands

Virtual GameBoy The Portable Nintendo Emulator 1996 Marcel de Kogel, Marat Fayzul-lin, Thierry Lescot, Hans de Goede.

The software operates by setting the internal timer to interrupt at the sample rate (200 Hz). At each timer interrupt the software enables the ADC via -CS line, it then sets the serial port to load one byte of data from the ADC. Once the data is loaded from the ADC the ADC is disabled via -CS. The data is then stored, displayed and processed as desired.

The components used are all commonly available, however, the invention is not particularly limited to any specific component.

The portable modular diagnostic medical system has been described. The system is portable in that it is based on a portable handheld Nintendo® Game Boy® device. The system is modular in that different pre-programmed cartridges having different diagnostic medical applications can be plugged into the Nintendo® Game Boy® device along with appropriate bio-acquisition module.

The device is simple to operate. In the preferred embodiments described, ECG waveforms can be stored in the RAM or displayed on the screen on-line in real time. This provides options for long term storage of the biological data, review, printout or transmission of the stored data to the computer.

The foregoing describes only one embodiment of the present invention, and modifications obvious to those skilled in the art can be made thereto without departing from the scope of the present invention.

What is claimed is:

1. A portable and multipurpose medical device for biological signals acquisition, display and biological data storage, said medical device comprising:

a preprogrammed and a biological signals acquisition module comprising:
a housing;
a connector partially disposed within the housing;
a read only memory (ROM) for storage of the program which has been preprogrammed;
a random access memory (RAM) for storage of acquired data;
a ROM-RAM parallel interface;
a plurality of biological sensors for measuring at least two biological parameters of the group comprising multilead ECG, FECG, EEG, EMG, oximetry, blood pressure, respiration, temperature, phonocardiogram, tokolytic, blood glucose, $pCO_2$, $pO_2$ and pacemaker pulses, at least one biological sensor of said plurality of biological sensors being an ECG sensor for monitoring said ECG;

an electrically isolated analog circuit for amplifying and pre-conditioning biological signals from the plurality of the biological sensors;

an ECG amplifier for amplifying an ECG signal from said sensor for monitoring said ECG;

a digital circuit for digitizing the biological signal and for sending the biological data through the connector of said preprogrammed and a biological signals acquisition module for storing the collected biological data in the RAM; and, a portable device comprising:
 a second housing;
 a slot connector being provided for insertion of the preprogrammed module;
 a display screen being provided on the second housing for displaying the acquired data; and,
 a joy pad and control buttons disposed within the second housing to control data acquisition options, horizontal and vertical scales of the display screen.

2. The portable and multi-purpose medical device for biological signals acquisition, display and biological data storage according to claim 1, wherein the portable device is a hand-held game device.

3. The portable and multi-purpose medical device for biological signals acquisition, display and biological data storage according to claim 1, wherein said electrically isolated analog circuit includes an isolated section, a non-isolated section with an isolation barrier therebetween, the isolated section being isolated from the input-output port of the display screen.

4. The portable and multi-purpose medical device for biological signals acquisition, display and biological data storage according to claim 3, wherein the isolated section receives the signals from said plurality of biological sensors and amplifies and preconditions the signals into data specific to the signal type prior to transmitting the data through the isolation barrier.

5. The portable and multi-purpose medical device for biological signals acquisition display and biological data storage according to claim 3, wherein the non-isolated section receives the data transmitted through the isolation barrier and prepares the data for transmission to an input/output port of the display screen via an input/output interface in said first housing and cable means to the input/output of the display screen in said second housing.

6. The portable and multi-purpose medical device for biological signals acquisition, display and biological data storage according to claim 1, wherein said ECG amplifier comprises a high-input impedance front stage voltage follower, an instrumentation amplifier, a high pass filter, an additional amplification stage and a low pass anti-aliasing filter.

7. A portable and multipurpose medical device for biological signals acquisition, display and biological data storage, said medical device comprising:
 a preprogrammed cartridge comprising:
  a first housing;
  a connector partially disposed within said housing;
  a read only memory (ROM) for storing software preprogrammed on said preprogrammed cartridge;
  a random access memory (RAM) for storage of acquired data; and,
  a ROM-RAM parallel interface;
 a portable device comprising:
  a second housing;
  a slot connector for insertion of said preprogrammed cartridge;
  a display screen on said second housing for displaying the acquired data; and,
  a joy pad and control buttons within said second housing for controlling data acquisition options, horizontal and vertical scales of said display screen; and,
 a biological signals acquisition module comprising:
  a third housing;
  a plurality of biological sensors for measuring at least two biological parameters of the group comprising multilead ECG, FECG, EEG, EMG, oximetry, blood pressure, respiration, temperature, phonocardiogram, tokolytic, blood glucose, $pCO_2$, $pO_2$ and pacemaker pulses, at least one biological sensor of said plurality of biological sensors being an ECG sensor for monitoring said ECG;
  an analog circuit for amplifying and pre-conditioning biological signals from said plurality of the biological sensors;
  an ECG amplifier for amplifying an ECG signal from said sensor for monitoring said ECG;
  an input/output interface for connecting said third housing to said second housing; and,
  a digital circuit for digitizing the biological signal and for sending the biological data through said connector of said preprogrammed cartridge for storing the collected biological data in the RAM of said first housing.

8. The portable and multi-purpose medical device for biological signals acquisition, display and biological data storage according to claim 7, wherein the portable device is a hand-held game device.

9. The portable and multi-purpose medical device for biological signals acquisition, display and biological data storage according to claim 7, wherein said analog circuit includes an isolated section, a non-isolated section with an isolation barrier therebetween, the isolated section being isolated from the input-output port of the display screen.

10. The portable and multi-purpose medical device for biological signals acquisition, display and biological data storage according to claim 9, wherein the isolated section receives the signals from said plurality of biological sensors and amplifies and preconditions the signals into data specific to the signal type prior to transmitting the data through the isolation barrier.

11. The portable and multi-purpose medical device for biological signals acquisition, display and biological data storage according to claim 9, wherein the non-isolated section receives the data transmitted through the isolation barrier and prepares the data for transmission to an input/output port of the display screen via an input/output interface in said first housing and cable means to the input/output of the display screen in said second housing.

12. The portable and multi-purpose medical device for biological signals acquisition, display and biological data storage according to claim 7, wherein said ECG amplifier comprises a high-input impedance front stage voltage follower, an instrumentation amplifier, a high pass filter, an additional amplification stage and a low pass anti-aliasing filter.

* * * * *